(12) United States Patent
Bresco Torras et al.

(10) Patent No.: US 10,004,385 B2
(45) Date of Patent: Jun. 26, 2018

(54) OBLIQUE TIP ENDOSCOPE WITH ZERO DEGREE FIELD ANGLE

(71) Applicant: COVIDIEN LP, Mansfield, MA (US)

(72) Inventors: Pere Bresco Torras, Barcelona (ES); Maria Degollada Bastos, Barcelona (ES); Juan Carles Mateu Prununosa, Barcelona (ES); Angel Guerra Garcia, Barcelona (ES); Mireille Akilian, Somerville, MA (US); Allen An, Winchester, MA (US); Nikolai Begg, Wayland, MA (US)

(73) Assignee: COVIDIEN LP, Mansfield, MA (US)

( * ) Notice: Subject to any disclaimer, the term of this patent is extended or adjusted under 35 U.S.C. 154(b) by 14 days.

(21) Appl. No.: 15/055,126

(22) Filed: Feb. 26, 2016

(65) Prior Publication Data

US 2016/0249784 A1 Sep. 1, 2016

Related U.S. Application Data

(60) Provisional application No. 62/121,814, filed on Feb. 27, 2015.

(51) Int. Cl.
*A61B 1/00* (2006.01)
*A61B 1/015* (2006.01)
(Continued)

(52) U.S. Cl.
CPC ........ *A61B 1/00135* (2013.01); *A61B 1/0008* (2013.01); *A61B 1/0011* (2013.01); *A61B 1/00165* (2013.01); *A61B 1/00174* (2013.01); *A61B 1/00179* (2013.01); *A61B 1/00195* (2013.01); *A61B 1/012* (2013.01); *A61B 1/015* (2013.01); *A61B 1/018* (2013.01); *A61B 1/07* (2013.01); *A61B 1/12* (2013.01);
(Continued)

(58) Field of Classification Search
CPC ............ A61B 1/00064; A61B 1/00071; A61B 1/0008; A61B 1/00094; A61B 1/00096; A61B 1/00135; A61B 1/00142; A61B 1/00195; A61B 1/002; A61B 1/00163; A61B 1/00165; A61B 1/00167; A61B 1/0017; A61B 1/015; A61B 1/07; A61B 1/12; A61B 1/126; A61B 1/127; A61B 1/128; A61B 1/303; A61B 1/307; A61B 1/313; A61B 1/3132; A61B 1/317
USPC ........ 600/105, 114, 121–125, 127–130, 138, 600/156–159, 162–164
See application file for complete search history.

(56) References Cited

U.S. PATENT DOCUMENTS 4,911,148 A * 3/1990 Sosnowski ........... A61B 1/0051
600/136
6,193,666 B1 2/2001 Ouchi
(Continued)

FOREIGN PATENT DOCUMENTS

DE 1261275 2/1968
EP 2436300 4/2012
(Continued)

*Primary Examiner* — Ryan Henderson

(57) ABSTRACT

Systems, apparatuses, and methods are discussed herein for an endoscope. The endoscope has a distal tip with an oblique portion and a flat portion, the oblique portion defines a plane that forms an angle between and including 20 and 40 degrees to a central axis of the endoscope. A related sheath may have similar features at the distal tip.

10 Claims, 9 Drawing Sheets

(51) Int. Cl.

| | | |
|---|---|---|
| *A61B 1/12* | (2006.01) | |
| *A61B 1/317* | (2006.01) | |
| *A61B 1/012* | (2006.01) | |
| *A61B 1/018* | (2006.01) | |
| *A61B 1/07* | (2006.01) | |
| *G02B 23/24* | (2006.01) | |
| *G02B 23/26* | (2006.01) | |

(52) U.S. Cl.
CPC .............. *A61B 1/126* (2013.01); *A61B 1/317* (2013.01); *G02B 23/2423* (2013.01); *G02B 23/26* (2013.01); *G02B 23/2469* (2013.01)

(56) References Cited

U.S. PATENT DOCUMENTS

| | | | |
|---|---|---|---|
| 2003/0032860 | A1 | 2/2003 | Avni et al. |
| 2003/0125607 | A1* | 7/2003 | Boebel ............... A61B 1/00105 |
| | | | 600/136 |
| 2005/0085692 | A1 | 4/2005 | Kiehn et al. |
| 2006/0111612 | A1* | 5/2006 | Matsumoto ........ A61B 1/00089 |
| | | | 600/129 |
| 2007/0118014 | A1 | 5/2007 | Fuert et al. |
| 2007/0135682 | A1 | 6/2007 | Moriyama et al. |
| 2008/0214895 | A1 | 9/2008 | Campos |
| 2011/0071349 | A1* | 3/2011 | Drontle .............. A61B 1/00165 |
| | | | 600/106 |

FOREIGN PATENT DOCUMENTS

| | | | | |
|---|---|---|---|---|
| EP | 2436300 A1 * | 4/2012 | ......... | A61B 1/00096 |
| JP | 2013188375 | 9/2013 | | |

\* cited by examiner

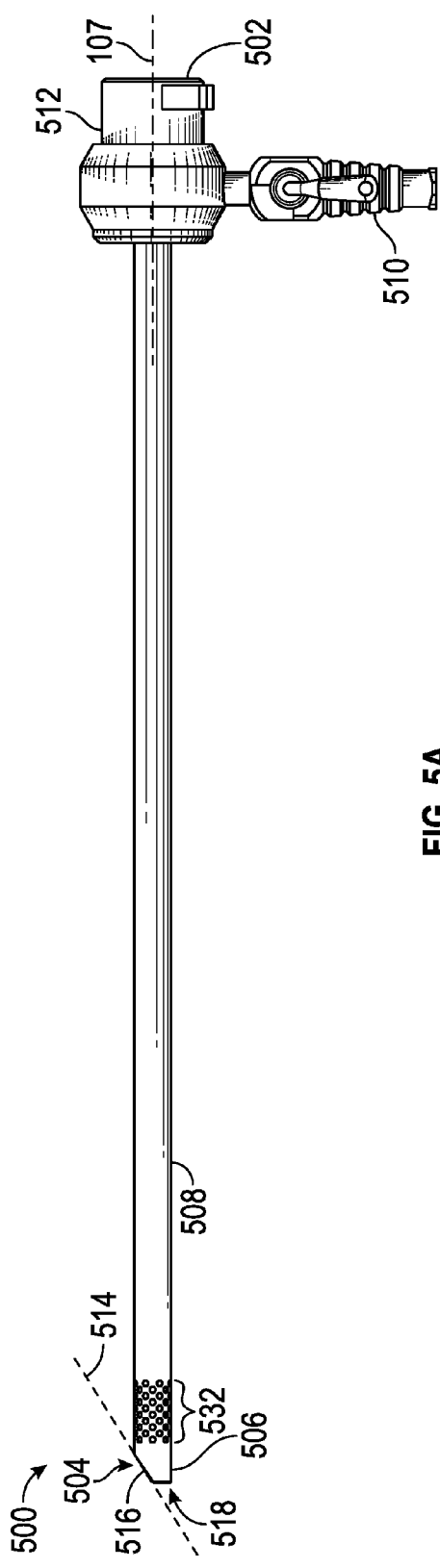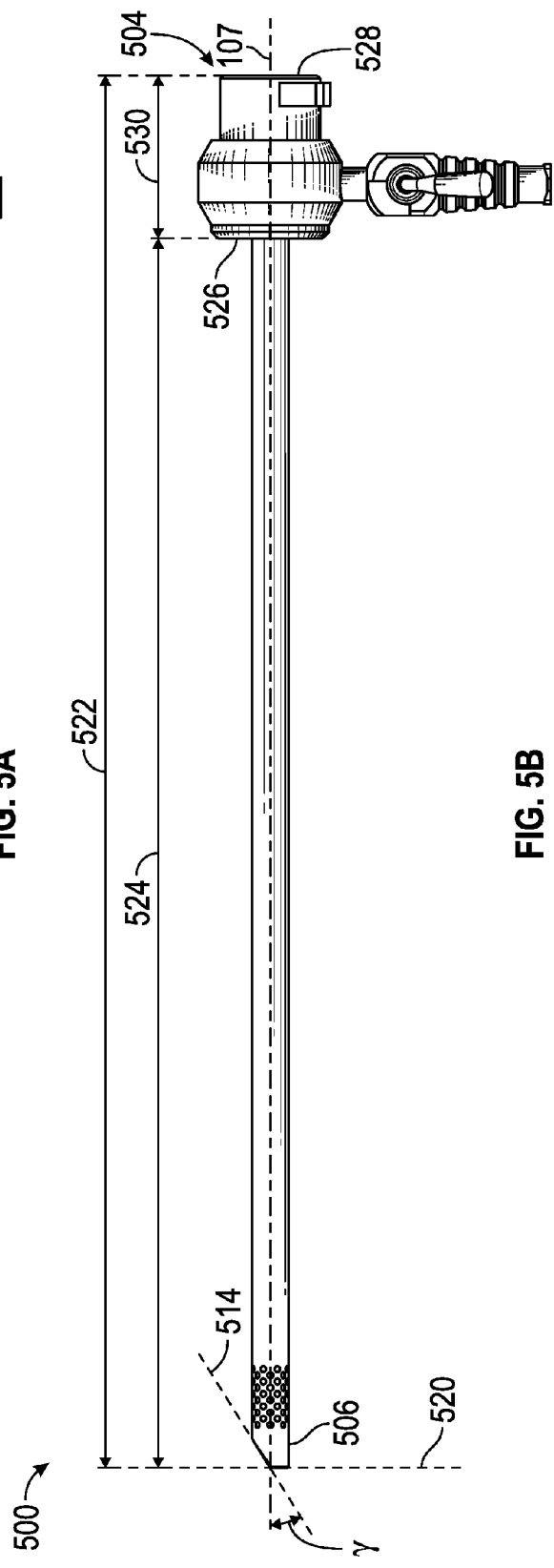
FIG. 5A
FIG. 5B

FIG. 6A  FIG. 6C

OBLIQUE TIP ENDOSCOPE WITH ZERO DEGREE FIELD ANGLE

CROSS-REFERENCE TO RELATED APPLICATIONS

This application claims the benefit of provisional application Ser. No. 62/121,814 filed Feb. 27, 2015, and titled, "Oblique tip endoscope with zero degree field angle," which provisional application is incorporated by reference herein in its entirety as if reproduced in full below.

BACKGROUND

Medical endoscopes are inserted into the patient either through an orifice, incision, or other entry point. In many applications, the critical dimension of the orifice is smaller than the diameter of the endoscope cross-section, which means the orifice expands to accommodate the endoscope. Depending on the tissue structure, mechanical properties, and proximity to nerves, the deformation caused by insertion of the endoscope may result in tissue trauma and pain.

To reduce pain, many times the diameter of the endoscope is reduced; however, the diameter must be large enough to contain the functional components of the endoscope, and as such the diameter is often practically limited.

BRIEF DESCRIPTION OF THE DRAWINGS

For a detailed description of various embodiments, reference will now be made to the accompanying drawings in which:

FIGS. 5A and 5B show side elevation views of a sheath for an endoscope in accordance with certain embodiments of the present disclosure.

FIG. 6A shows a magnified partial-perspective view of a distal end of a sheath in accordance with certain embodiments of the present disclosure.

SUMMARY

Figure 1:
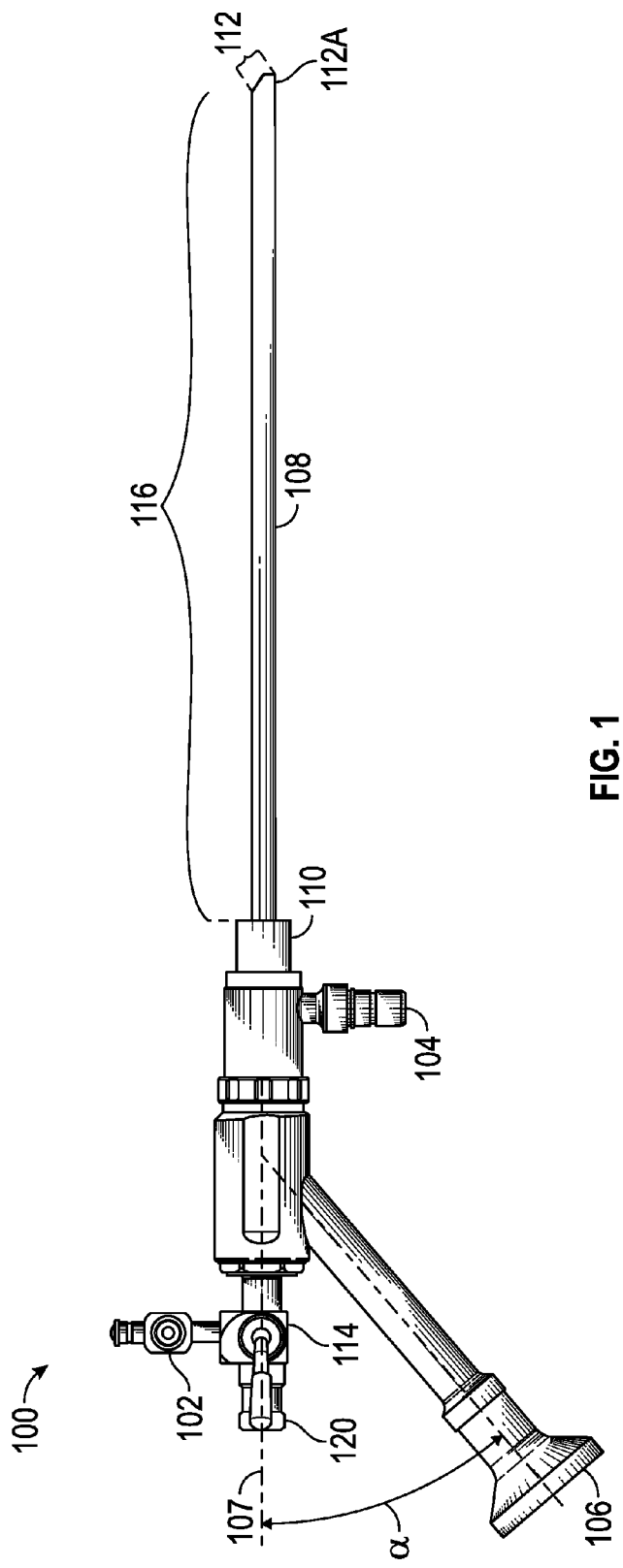
FIG. 1 shows a side elevation view of an endoscope in accordance with certain embodiments of the present disclosure.

An example embodiment is an endoscope comprising: an elongated shaft that defines a central axis, a proximal end, and a distal tip, the elongated shaft defines a cross-section along a portion of the elongated shaft; a first portion of the distal tip, wherein the first portion defines a first plane that forms an angle of between and including 20 and 40 angular degrees to the central axis; and a second portion of the distal tip, wherein the second portion defines a second plane that is perpendicular to the central axis. The example endoscope further comprises: a first transition area on a first side of the distal tip between the first portion and the second portion, the first transition area smoothly varying between the first portion and the second portion; a second transition area on a second side of the distal tip opposite the first side, the second transition area smoothly varying between the first portion and the second portion; and a view port coupled to the proximal end of the elongated shaft, the view port extends away from the central axis. The example endoscope further comprise: a first channel within the elongated shaft that terminates at the first portion; a second channel within the elongated shaft that terminates at the second portion, the second channel fluidly isolated from the first channel along a length of the elongated shaft; and a visualization conduit that extends through the view port and the second channel, the visualization conduit optically exposed at the second plane such that a viewing angle through the visualization conduit is parallel to the central axis.

Other example embodiments are an endoscope and sheath system. The example endoscope comprises: an endoscope elongated shaft that defines an endoscope central axis, an endoscope proximal end, and an endoscope distal tip, the endoscope elongated shaft defines a cross-section along a portion of the endoscope elongated shaft; an endoscope first portion of the endoscope distal tip defines a first plane that forms an angle of between and including 20 and 40 angular degrees to the endoscope central axis; an endoscope second portion of the endoscope distal tip defines a second plane that is perpendicular to the endoscope central axis; and an endoscope first transition area on a first side of the endoscope distal tip between the endoscope first portion and the endoscope second portion, the endoscope first transition area smoothly varying between the endoscope first portion and the endoscope second portion. The example endoscope further comprises: an endoscope second transition area on a second side of the endoscope distal tip opposite the first side, the endoscope second transition area smoothly varying between the endoscope first portion and the endoscope second portion; a view port couple to the proximal end of the endoscope elongated shaft, the view port extends away from the endoscope central axis; a first channel within the endoscope elongated shaft that terminates at the endoscope first portion; a second channel within the endoscope elongated shaft that terminates at the endoscope second portion, the second channel fluidly isolated from the first channel along a length of the endoscope elongated shaft; and a visualization conduit that extends through the view port and the second channel, the visualization conduit optically exposed at the second plane such that a viewing angle through the visualization conduit is parallel to the endoscope central axis. The example system further includes a sheath comprising: a sheath elongated shaft that defines a sheath central axis, a sheath proximal end, and a sheath distal tip, the sheath elongated shaft defines a circular cross-section along a portion of the sheath elongated shaft; a sheath first portion of the sheath distal tip defines a third plane parallel to the first plane; a sheath second portion of the sheath distal tip defines a fourth plane parallel to the second plane; and a sheath first transition area on a first side of the sheath distal tip between the sheath first portion and the sheath second portion, the sheath first transition area smoothly varying between the sheath first portion and the sheath second portion. The example sheath further comprises: a sheath second transition area on a second side of the sheath distal tip opposite the first side, the sheath second transition area smoothly varying between sheath first portion and the sheath second portion; a plurality of apertures disposed a sheath distal end of the sheath elongated shaft proximate to the sheath first portion; and an insertion port at the sheath proximal end of the sheath elongated shaft, the endoscope elongated shaft telescoped through the sheath insertion port.

Example methods comprise: positioning a distal tip of an endoscope to abut an aperture into a patient's body, a distal tip of the endoscope having a first feature that defines a first plane that forms an angle with a central axis of the endoscope, and a second feature that defines a second plane perpendicular to the central axis of the endoscope; inserting the distal tip of the endoscope through the aperture into the patient's body, wherein insertion force of the distal tip into the aperture is less than 80% of an insertion force of an endoscope with a blunt front and having a same outer dimension of an elongated shaft as the endoscope having the first and second features; and visualizing an interior portion of the patient's body at a viewing angle that is parallel to the central axis.

Other example methods comprise: positioning a distal tip of an endoscope to abut an aperture into a patient's body, a distal tip of the endoscope having a first portion that defines a first plane that forms an angle between and including 20 and 40 angular degrees with a central axis of the endoscope, and a second feature that defines a second plane perpendicular to the central axis of the endoscope; inserting the distal tip of the endoscope through the aperture into the patient's body; and visualizing an interior portion of the patient's body at a viewing angle that is parallel to the central axis.

Yet still other example methods comprise assembling an endoscope by: obtaining an outer tube that comprises: a first central axis, a first proximal end, and a first distal tip; a first portion at the first distal tip defines a first plane that forms an angle of between and including 20 and 40 angular degrees to the first central axis; and a second portion at the first distal tip that defines a second plane perpendicular to the first central axis; obtaining an inner tube that comprises: a second central axis, a second proximal end, and a second distal tip; a first portion at the second distal tip defines a third plane that forms an angle of between and including 20 and 40 degrees to the second central axis; and a second portion at the second distal tip that defines a fourth plane perpendicular to the second central axis; telescoping the inner tube into the outer tube until the first and third planes are coplanar and two channels are defined within the outer tube, the first channel within the inner tube, and the second channel defined between the inner tube and an inside surface of the outer tube; telescoping within the second channel a visualization conduit; coupling the visualization conduit to an eyepiece in viewing port; and optically exposing the visualization conduit at the first distal end with viewing angle parallel to the first central axis.

Definitions

Certain terms are used throughout the following description and claims to refer to particular system components. As one skilled in the art will appreciate, different companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

An "elliptical cross-section" shall mean a closed curve on a plane surrounding two focal points such that the sum of the distances to the two focal points is constant for every point on the curve. A circular cross-section is a special case of the elliptical cross-section where the two focal points are collocated.

A "visualization conduit" shall mean a medium through which visualization takes place during use of an endoscope. The visualization conduit may be, for example, a rod lens or an optical fiber bundle. The fact that the visualization conduit can carry illumination to the viewing area shall not obviate the status as a visualization conduit.

A "light fiber bundle" shall mean a plurality of optical fibers through which light is carried to illuminate an area of visualization (the visualization through a separate visualization conduit). The fact that each optical fiber can theoretically be used to provide visualization, albeit of low resolution, shall not obviate the status a light fiber bundle (individually or as a group) as a light fiber bundle.

A "combination device," shall mean the device created when an endoscope is telescoped (disposed) in a sheath, in order to differentiate the combination device from the unsheathed endoscope devices discussed herein. In practice, it is appreciated that the combination device may be referred to as an "endoscope" or an "endoscope device."

An "insertion force" shall mean the force to insert a distal tip of an endoscope through a one inch diameter, 0.125 inch thickness medical grade rubber membrane with a prepunched 1 millimeter (mm) diameter hole.

"Blunt front" shall mean an endoscope or sheath whose distal tip has only a single feature, and that single feature forms a plane perpendicular to a central axis of the endoscope or sheath.

"Coplanar," with respect to features of endoscopes, sheaths, or components that are assembled to construct an endoscope, shall also include parallel planes defined by the respective features where the perpendicular distance between the planes is 0.5 millimeters or less.

DETAILED DESCRIPTION

The following discussion is directed to various embodiments. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The apparatuses, systems, and methods discussed herein relate to an endoscope comprising an oblique or angled feature on the distal end (hereafter oblique portion), a sheath comprising an oblique or angled feature on the distal end (hereafter oblique portion), and a combination of the endoscope and sheath where the endoscope is telescoped (disposed) in the sheath to form a combination device. The various example systems are also directed to endoscopes and related devices with features that reduce insertion force, and therefore reduce trauma, pain, and recovery time for the patient. More particularly, the embodiments discussed herein have an oblique portion on the distal end that results in a gradual dilation of the orifice during insertion, which reduces trauma. However, to ensure proper visualization for endoscopes, the distal end of the endoscope also comprises a feature that defines a plane perpendicular to the long axis of the endoscope (hereafter flat portion) such that the view of a visualization conduit is along the long axis of the endoscope. That is, the viewing angle is approximately a zero degree field angle. The oblique portion at the distal tip eases insertion of the scope through an aperture in a patient's body and therefore reduces the force employed for insertion.

The figures discussed below illustrate various embodiments of endoscopes, sheaths, and combination devices. The various features comprising and defining these devices are discussed on multiple figures in different perspective views and scales, each feature is identified in the first instance of its appearance in a figure and may be further referenced in other figures but not explicitly identified due to the perspective of the other figure or figures.

FIG. 1 shows a side elevation view of an endoscope 100 in accordance with example embodiments of the present disclosure. In particular, FIG. 1 shows endoscope 100 comprising a central axis 107, a proximal end 120, a distal end defined by a distal tip 112, an inflow port 102, and an optics port 104 through which light is provided to a light fiber bundle (not visible in FIG. 1). In the example embodiment, the inflow port 102 and the optics port 104 may each extend perpendicularly from the central axis 107 of the endoscope 100, but other relationships are contemplated. The endoscope 100 may also comprise a viewing port 106 that may form an angle α of about 40 angular degrees as measured from the central axis 107 of the endoscope 100. The viewing port 106 has disposed therein a visualization conduit that extends from the viewing port 106 to the distal tip 112. The visualization conduit is not visible in the view of FIG. 1, but is discussed in greater detail below. The endoscope further comprises an elongated shaft 108 having a length 116 from a proximal end 110 of the elongated shaft 108 to the end 112A of the distal tip 112. In the example embodiment, the length 116 is about 226.4 millimeters (mm), but longer and shorter lengths are also contemplated. The elongated shaft 108 defines within an interior volume a first channel (not visible in FIG. 1) that extends along the central axis 107 of the endoscope 100. The elongated shaft 108 is coupled to an insertion valve 114, and in use various tools (e.g., shavers, ablation devices) may be telescoped into the first channel of the elongated shaft 108 through the insertion valve 114.

Figure 2:
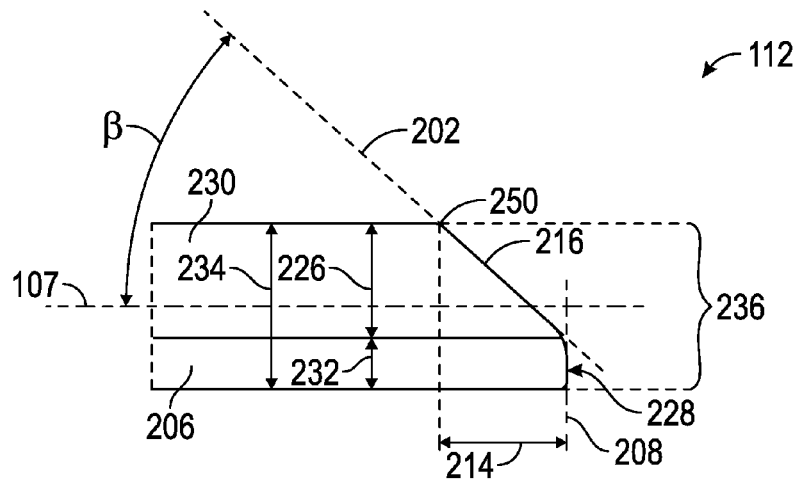
FIG. 2 shows a schematic side elevation view of the distal end of the endoscope of FIG. 1 in accordance with certain embodiments of the present disclosure.

FIG. 2 shows a cross-sectional elevation view of the distal tip 112 of the endoscope 100. In particular, the distal tip 112 comprises a feature in the form of an angled or oblique portion 216 that defines a plane. In the view of FIG. 2 the plane defined by the oblique portion 216 is perpendicular the page, and thus the plane is visible only as line 202. The plane defined by the oblique portion 216 (visible as line 202) forms an angle β with the central axis 107 of the endoscope, which angle β may be between about 20 and 40 angular degrees in some cases, in other cases may be between about 30 and 34 angular degrees, and in yet still other cases may be about 32 angular degrees. The distal tip 112 also comprises a flat portion 228 that defines a second plane. In the view of FIG. 2 the second plane defined by the flat portion 228 is perpendicular the page, and thus the plane defined by the flat portion 228 is visible only as line 208. The plane defined by the flat portion 228 (visible as line 208) is perpendicular to the central axis 107 of the elongated shaft 108. In an example embodiment, the length 214 may be about 5.5 mm, but selection of the angle β affects the length 214. The distal tip 112 further comprises a length 214 measured from a proximal portion 250 of the oblique feature 216 to the flat portion 228. The distal tip 112 also defines a height 236 measured perpendicular to the central axis 107, and a width (delineated with respect to FIG. 3C, discussed more below). The endoscope 100 may also define two interior channels, the first indicated by 230 and the second indicated by 206.

Figure 3A:
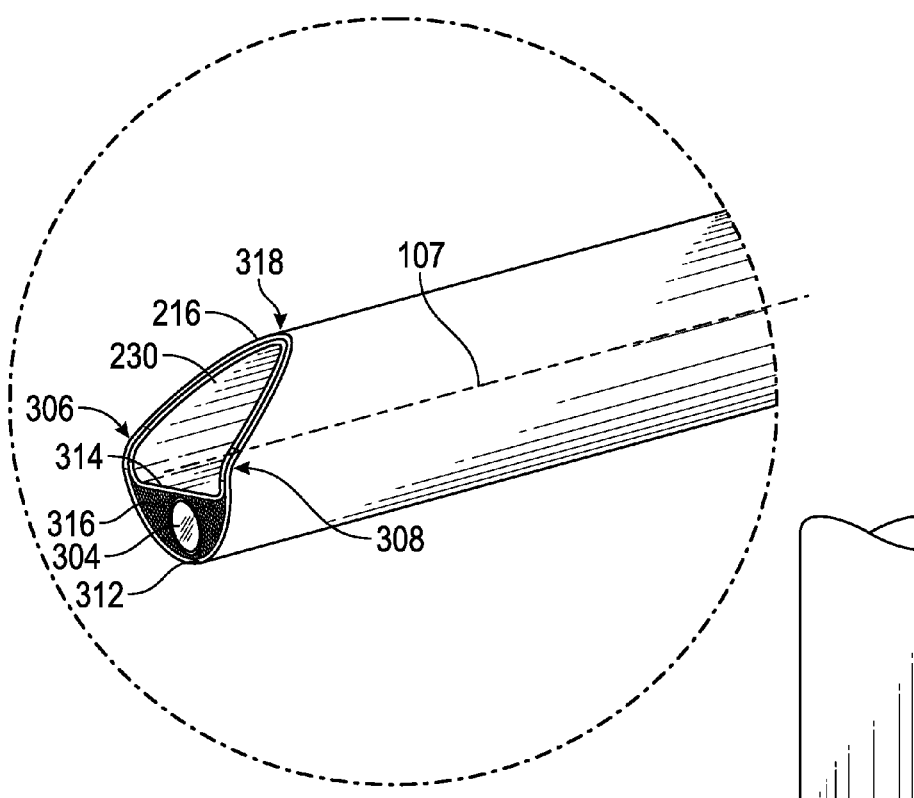
FIG. 3A shows a magnified partial-perspective view of the distal end of an endoscope in accordance with certain embodiments of the present disclosure.
Figure 3C:
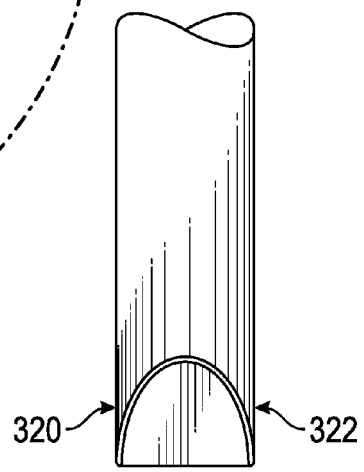
FIG. 3C shows an overhead view, of a distal tip of an endoscope in accordance with certain embodiments of the present disclosure.
Figure 3B:
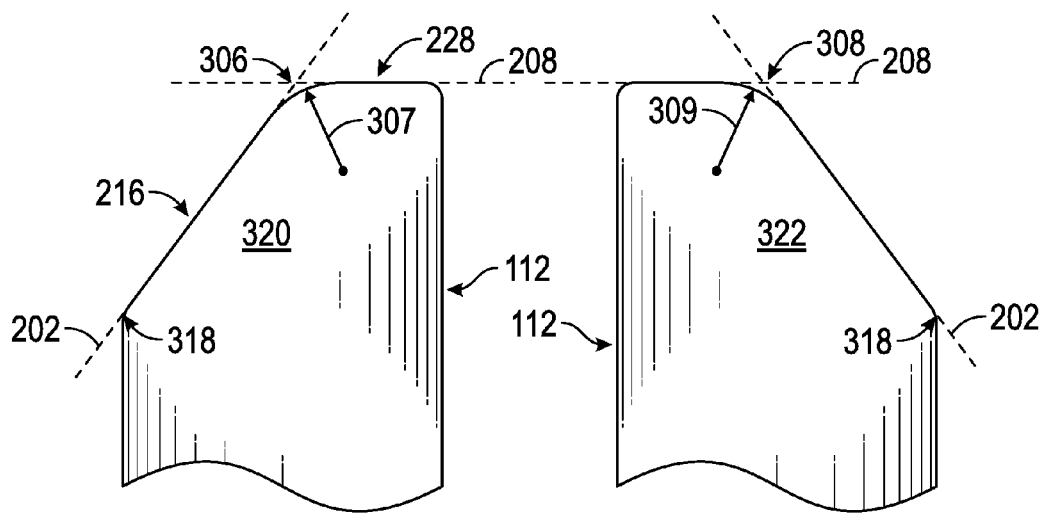
FIG. 3B shows and left and right side elevation views.

FIG. 3A shows elevation views of the distal end of the endoscope 100. FIG. 3B shows left and right side elevation views of the distal tip 112 of the endoscope 100. FIG. 3C shows a top elevation view of the distal tip 112. FIGS. 3A-3C are discussed interchangeably herein. The example endoscope comprises first channel 230 that runs parallel to the central axis 107. During use of the endoscope the first channel 230 may be employed for fluid flow and/or instrumentation. The first channel 230 at the distal tip 112 defines an upper smoothly curved surface 318, and a flat surface (straight portion) 314 opposite an apex of the curved surface 318. The distal tip 112 is defined, at least in part, by the oblique portion 216 and the flat portion 228. Between the oblique portion 216 and the flat portion 228 resides a first transition area 306 on a first side 320 of the distal tip 112. In example embodiments, the first transition area 306 smoothly varies between the oblique portion 216 and the flat portion 228. The distal tip 112 further comprises a second transition area 308 on a second side 322 of the distal tip 112, the second transition area 308 opposite first transition area 306. The second transition area 308 smoothly varies between the oblique portion 216 and the flat portion 228. In example embodiments, each transition area 306 and 308 defines a radius of curvature (i.e., radius of curvature 307 for transition area 306, and radius of curvature 309 for transition area 308 (FIG. 3B)). The radius of curvature for each transition area is discussed more below after introduction of the various outside dimensions of the elongated shaft 108 (in reference to FIG. 4). The upper smoothly curved surface 318 may also be referred to as a transition area.

Still referring to FIGS. 3A-3C, the second channel is defined by a smoothly curved surface 312 of the endoscope 100 and by the flat surface 314 of the first channel 230. In the example system shown, a visualization conduit 304 is disposed in the second channel parallel to the central axis 107. The visualization conduit 304 terminates in such a way that the viewing angle is parallel to the long central axis 107 (i.e., there is about a zero degree field viewing angle). For example, the visualization conduit 304 may terminate at or along (flush or nearly flush with) the plane defined by the flat portion 228 (visible as line 208 (FIGS. 2 and 3B)). Also disposed in the second channel are a plurality of optical fibers that make up the light fiber bundle 316.

Figure 4:
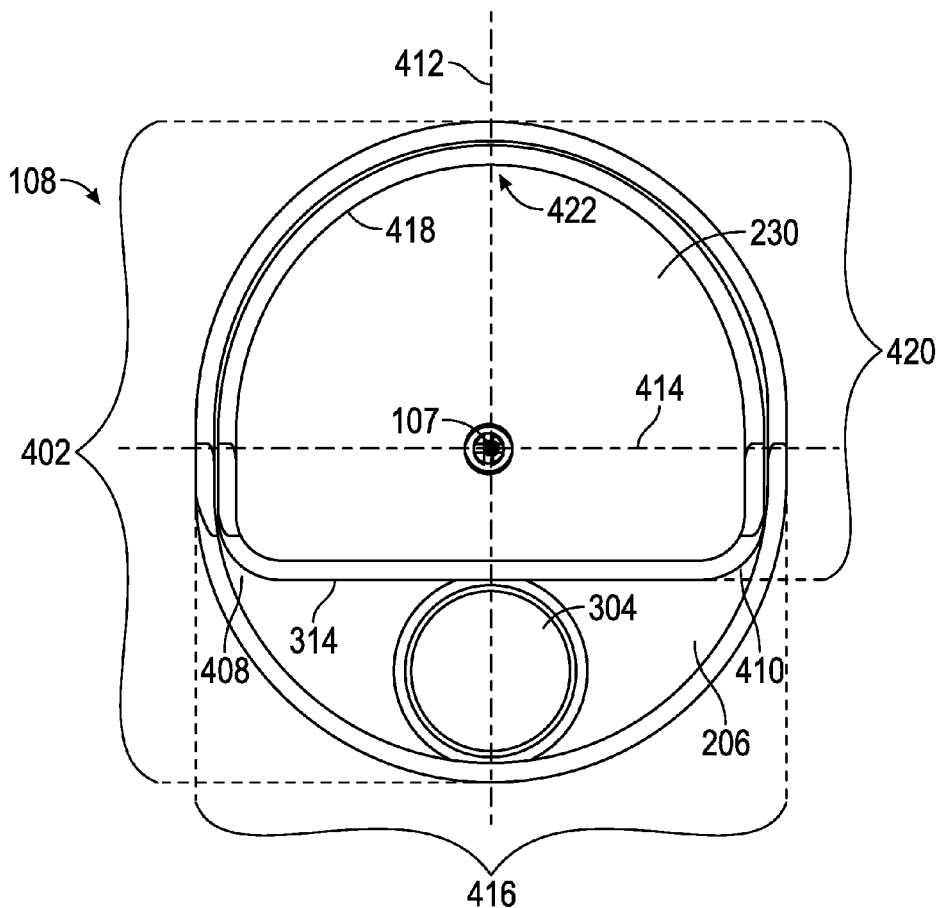
FIG. 4 shows an end elevation view of an endoscope in accordance with certain embodiments of the present disclosure.

FIG. 4 shows an end elevation view of the distal tip 112 of the endoscope 100 in FIG. 1. In particular, FIG. 4 shows a largest outer dimension 402 of the elongated shaft 108 measured perpendicularly to the central axis 107. A further outside dimension 416 is also shown, which is measured perpendicular to the largest outside dimension 402 and which may be equal to or smaller than the largest outside dimension 402. FIG. 4 further shows the visualization conduit 304 disposed equidistant in between a first side 408 and a second side 410 of the flat surface 314 of the second channel 206, but in other example cases the visualization conduit may be disposed favoring one side or another. Also shown are two axes 412 and 414, each of which pass through the central axis 107 and are perpendicular to the central axis 107 and to each other.

Referring simultaneously to FIGS. 1, 2, 3A-3C, and 4, which each show different views of the endoscope 100, the example endoscope 100 comprises elongated shaft 108 that defines a central axis 107, a proximal end 120, and a distal tip 112. The distal tip 112 includes an oblique portion 216 that defines a plane (shown as line 202) that forms an angle with respect to the central axis 107. The distal tip 112 also includes a flat portion 228 that defines a plane (shown as line 208) that is perpendicular to the central axis 107. The first transition area 306 is disposed on the first side 320 of the distal tip 112 between the oblique portion 216 and the flat portion 228, and the first transition area 306 smoothly varies between the oblique portion 216 and the flat portion 228. The example endoscope comprises the second transition area 308 on the second side 322 of the distal tip 112 opposite the first side 320, and the second transition area 308 smoothly varies between the oblique portion 216 and the flat portion 228. In an example embodiment, the viewing port 106 is coupled to the proximal end 110 of the elongated shaft 108 and the viewing port 106 extends away from the central axis 107. The first channel 230 within the elongated shaft 108 terminates at least in part at the oblique portion 216. The second channel 206 within the elongated shaft 108 terminates at the flat portion 228, and the second channel 206 is fluidly isolated from the first channel 230 along a length 116 of the elongated shaft 108.

In the example endoscope, the visualization conduit 304 extends through the viewing port 106 and the second channel 206, and is optically exposed at the second plane (shown as line 208) such that a viewing angle through the visualization conduit 304 is parallel to the central axis 107. In example embodiments, the elongated shaft 108 defines an oval or elliptical cross-section over at least a portion of the elongated shaft 108, and in some cases along the entire elongated shaft 108. As defined above, elliptical cross-section includes, as a special case, circular cross-sections, and thus in some cases the elongated shaft 108 may be circular over all or part of its length. The endoscope 100 may further comprise the plurality of optical fibers that make up a light fiber bundle 316 disposed within the second channel 206 along with the visualization conduit 304. The light fiber bundle 316 may be optically exposed at the second plane (shown as line 208), and likewise the light fiber bundle 316 is optically connected to the optics port 104. The elongated shaft 108 defines a largest outside dimension 402 measured perpendicularly to the central axis 107 (e.g., measured along axis 412), and the elongated shaft 108 defines a further outside dimension 416 also measured perpendicularly to the central axis 107 (e.g., measured along axis 414). The further outside dimension 416 may be equal to or smaller than the largest outside dimension 402.

Again, the example distal tip 112 comprises a plurality of transition areas, including a first transition area 306 that defines a first radius of curvature 307 between and including 8% and 20% of the largest outside dimension 402, and a second transition area 308 defines a second radius of curvature 309 between and including 8% and 20% of the largest outside dimension 402. In the example embodiment, the endoscope 100 further comprises a upper smoothly curved surface 318 on the oblique portion 216 between the first 306 and second 308 transition areas, the upper smoothly curved surface 318 smoothly varies from the plane defined by the oblique portion 216 to an outside diameter of the elongated shaft 108.

The example first channel 230 may comprise a "D" cross-sectional shape as shown in FIG. 4. The cross-sectional shape shown in FIG. 4 defines a flat surface 314 parallel to the further outside dimension 416, and a curved portion 418 coupled on each side 408, 410, to the flat surface 314. The first channel 230 has a height 420 measured from an apex 422 of the curved portion 418 to the flat surface 314. In some embodiments, the first channel 230 height 420 is greater than half of the largest outside dimension 402 of the elongated shaft 108, but smaller than an internal dimension 234 (FIG. 2) of the elongated shaft 108, as measured parallel to the largest outside dimension 402.

The example endoscope 100 discussed above may be employed using the methods discussed below alone or in combination with a sheath, and an example sheath is discussed below in FIGS. 5A-5C and 6A-6C.

FIG. 5A shows a side elevation view of a sheath 500 in accordance with certain embodiments of the present disclosure. In particular, the sheath 500 defines a proximal end 502 and a distal end 504, and the distal end 504 comprises a distal tip 506 (discussed in greater detail with respect to FIGS. 6A-6C). The sheath 500 comprises elongated shaft 508 that defines an interior channel (not visible in FIG. 5A, but discussed more below). In some embodiments, the interior channel, through which various instruments may be inserted for surgical procedures (e.g., the endoscope 100), may also be used for fluid flow. The interior channel may extend from a connector portion 512 on the proximal end 502 of the sheath 500 to the distal end 504. The connector portion 512 may be configured in various manners to couple to and/or enable telescoping of an endoscope.

The example sheath 500 comprises a fluid port 510 located in proximity to the proximal end 502. The fluid port 510, when the valve of the port is open, is in fluid communication with the interior channel defined by the elongated shaft 508, and thus fluid may flow into or out of the interior channel by way of the fluid port 510. The distal tip 506 may be defined by a plurality of features including an oblique portion 516 and a flat portion 518. The oblique portion 516 defines a plane. In the view of FIG. 5A the plane defined by the oblique portion 516 is perpendicular the page, and thus the plane is visible only as line 514. The plane defined by the oblique portion 516 (visible as line 514) forms an angle γ with the central axis 107 of the sheath 500, which angle γ may be between about 30 and 34 angular degrees, and in some embodiments may be about 32 angular degrees.

FIG. 5B shows a side elevation view of the example sheath 500. Referring simultaneously to FIGS. 5A and 5B, the flat portion 518 also defines a plane. In the view of FIG. 5B, the plane defined by the flat portion 518 is perpendicular the page, and thus the plane is visible only as line 520. The plane defined by the flat portion 518 (visible as line 520) is perpendicular to the central axis 107 of the elongated shaft 508. In example embodiments, the elongated shaft 508 may comprise a plurality of apertures 532 disposed circumferentially around at least a portion of the circumference of the shaft and along a predetermined length of the elongated shaft 508, where the predetermined length may be less than an overall length (shown and discussed in FIG. 5B). The plurality of apertures 532 may comprise various shapes, sizes, and locations, including uniform and non-uniform arrays.

Referring specifically to FIG. 5B, example sheath 500 comprises an overall length 522 extending from the distal tip 506 to the proximal end 502, and a shaft length 524. The shaft length 524 may be defined as extending from the distal end 526 of the connector portion 512 to the distal tip 506. The connector portion 512 comprises a length 530 measured from the distal end 526 of the connector 512 to the proximal end 502 along the central axis 107. In example embodiments, the sheath 500 may have a length 522 of about 225.6 mm, a shaft length 524 of about 204.2 mm, and a connector portion 512 length 530 of about 25 mm. Longer and short lengths are also contemplated.

Figure 6B:
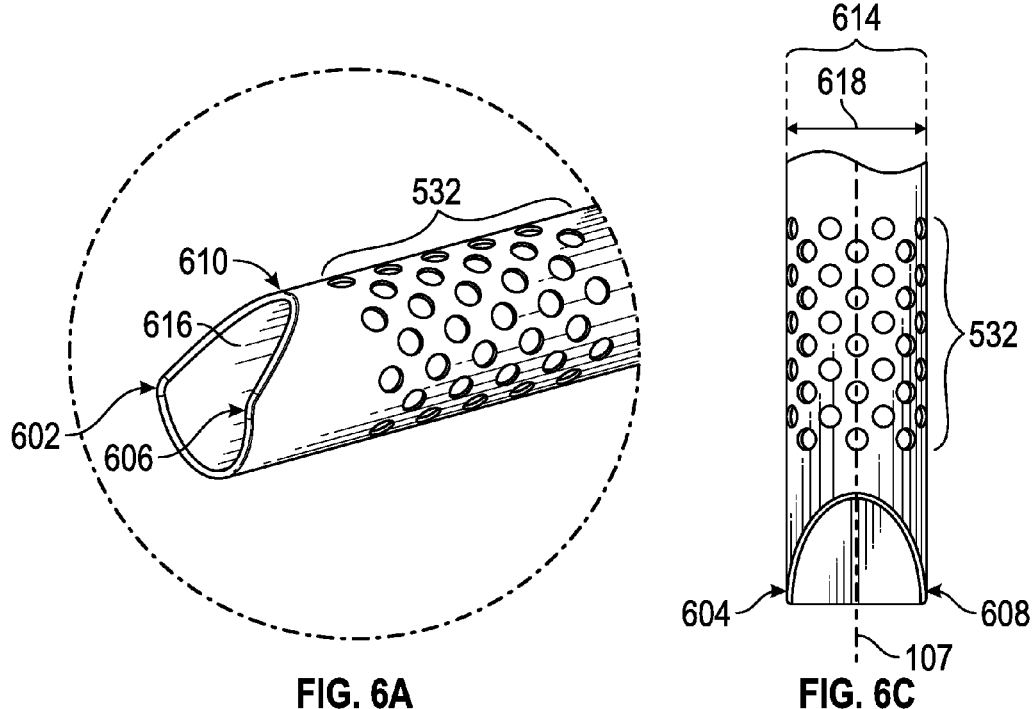
FIG. 6B shows a side elevation view, and 6C shows an overhead view, of a distal tip of a sheath in accordance with certain embodiments of the present disclosure.
Figure 6B:
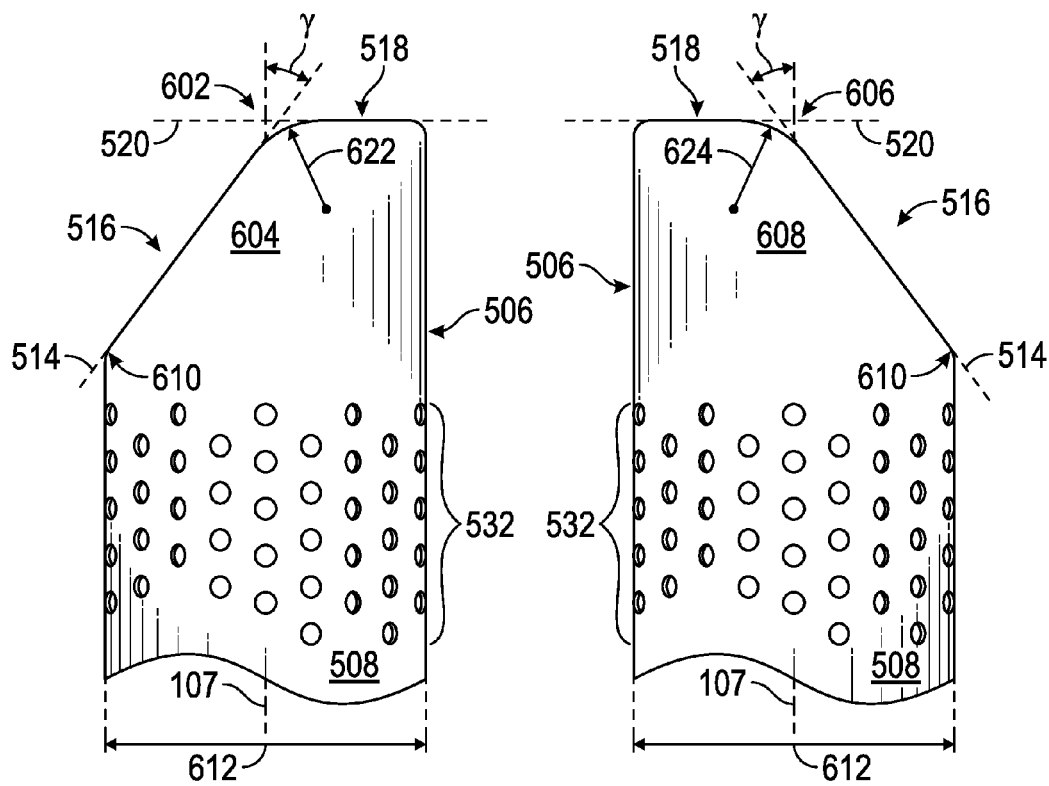

FIG. 6A shows a magnified partial-perspective view of the distal tip 506 of the sheath 500. FIG. 6B shows left and right elevation views of the distal tip 506 of the sheath 500. FIG. 6C shows an overhead view of the distal tip 506 of the sheath 500. FIGS. 6A-6C are discussed inter interchangeably herein. In an example embodiment, the distal tip 506 comprises the oblique portion 516 and flat portion 518. Oblique portion 516 defines a plane, and in the view of FIG. 6B the plane defined by the oblique portion 516 is visible as a line 514. Flat portion 518 likewise defines a plane, and in the view of FIG. 6B the plane defined by the flat portion 518 is visible as a line 520. The distal tip 506 further comprises a first transition area 602 on a first side 604 of the distal tip 506 between the oblique portion 516 and the flat portion 518. The first transition area 602 smoothly varies between the oblique portion 516 and the flat portion 518. The second transition area 606 is located on a second side 608 opposite the first side 604, and the second transition area 606 smoothly varies between the oblique portion 516 and the flat portion 518.

Referring simultaneously to FIGS. 5A-5B and 6A-6C, the example sheath 500 comprises elongated shaft 508 that defines a central axis 107, a proximal end 502, and a distal tip 506. The elongated shaft 508 defines a largest outside dimension 612 along a portion of the elongated shaft 508. The oblique portion 516 of the distal tip 506 defines a plane (visible as line 514 in FIG. 6B) that forms an angle γ, the angle γ being between and including about 20 and about 40 angular degrees to the central axis 107. In some cases, the angle γ may be between and including about 30 to about 34 angular degrees, and in other cases the angle may be about 32 angular degrees. The first transition area 602 resides on the first side 604 of the distal tip 506 between the oblique portion 516 and the flat portion 518, with the first transition area 602 smoothly varying between the oblique portion 516 and the flat portion 518. The second transition area 606 resides on the second side 608 of the distal tip 506 opposite the first side 604, the transition area 606 smoothly varying between oblique portion 516 and the flat portion 518. The first transition area 602 defines a radius of curvature 622 between and including 8% and 20% of the largest outside dimension 612, and the transition area 606 likewise defines a radius of curvature 624 between and including 8% and 20% of the largest outside dimension 612. In an embodiment, an inner dimension 618 of the sheath 500 may be about 5.3 mm. The example distal tip 506 may also comprise a third transition area 610 on the oblique portion 516 between the first 602 and second transition 606 areas, the third transition area 610 smoothly varying from the plane defined by the oblique portion 516 (visible as line 514 in FIG. 6B) to a largest outside dimension 612 of the elongated shaft 108. In example sheaths where the cross-sectional shape of the sheath is elliptical (and the focal points are not collocated), a second (further) outside dimension 614, measured perpendicular to the largest outside dimension 612, may be equal to or less than the largest outside dimension 612.

In example sheaths, an insertion port 528 may be part of the connector portion 512 at the proximal end 502 of the elongated shaft 108, and the insertion port 528 may be configured to couple to a proximal end of an endoscope (e.g., endoscope 100) when the endoscope is telescoped through the insertion port 528.

Figure 7A:
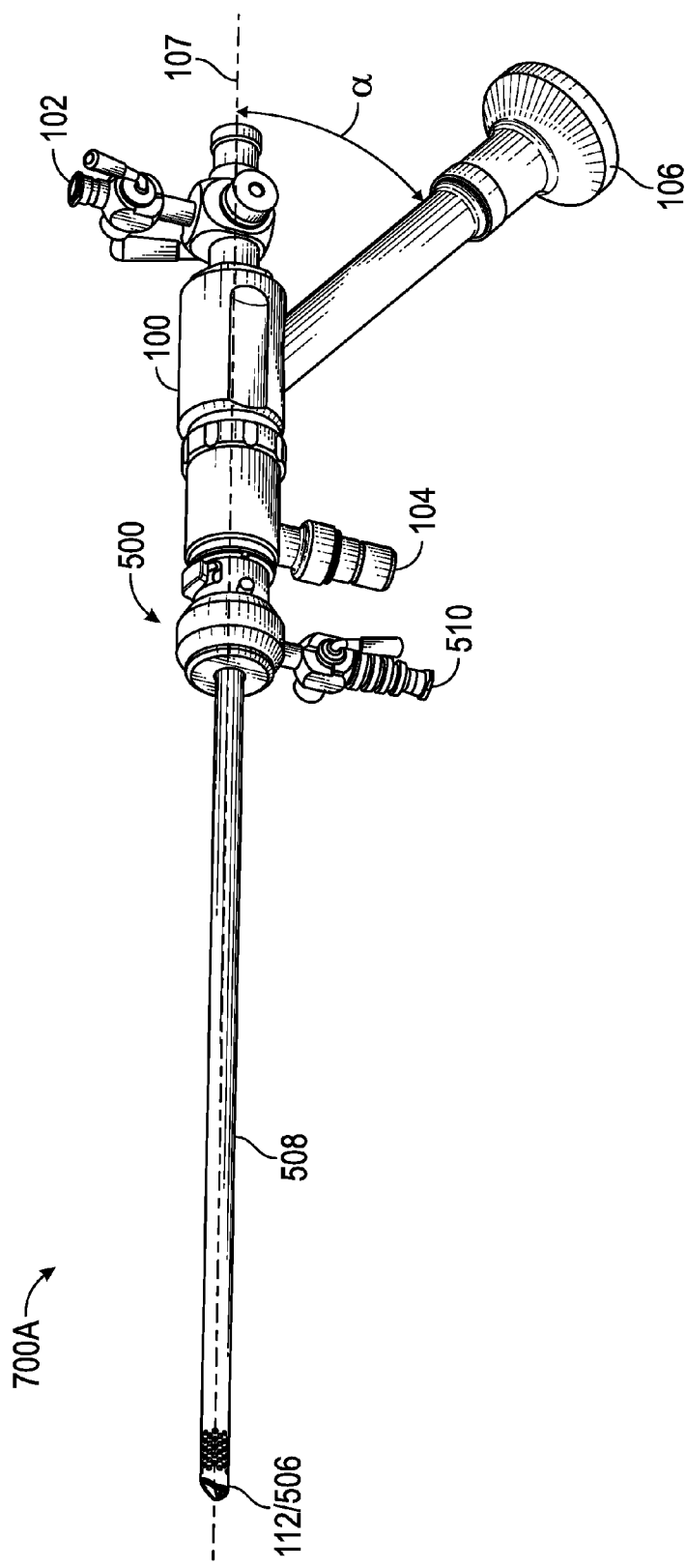
FIG. 7A shows a perspective view of an endoscope telescoped in a sheath in accordance with certain embodiments of the present disclosure.
Figure 7B:
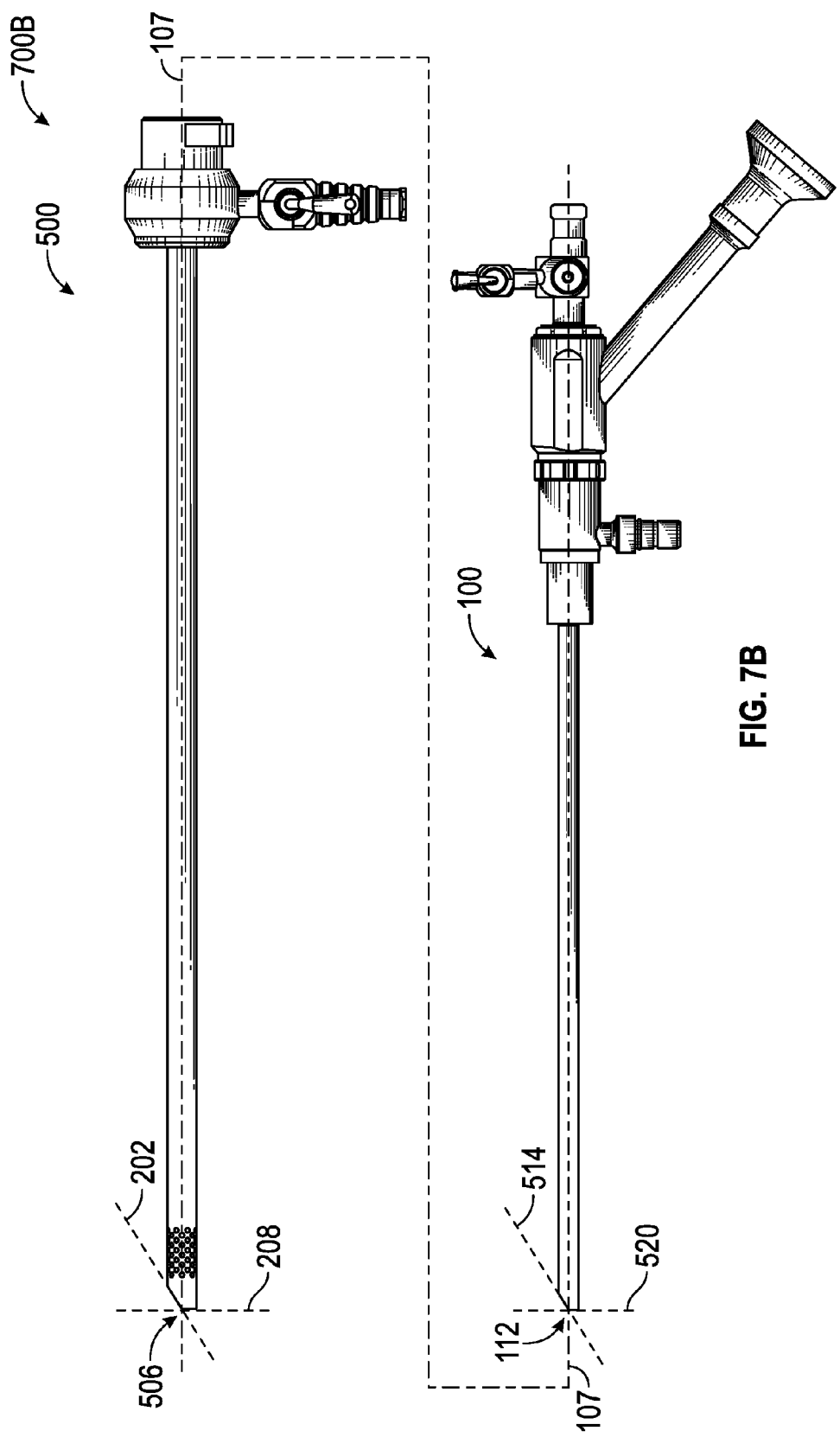
FIG. 7B shows an exploded perspective view of a sheath and an endoscope before the endoscope is telescoped in the sheath in accordance with certain embodiments of the present disclosure.

FIG. 7A shows a perspective view of an endoscope telescoped in a sheath. In particular, in the combination device 700A the example endoscope 100 is telescoped in an example sheath 500. FIG. 7B shows an exploded view of each device 100, 500, separately with the central axis 107 along which both devices are aligned. When telescoped (as in the embodiment as shown in FIG. 7A) the planes formed by the oblique portions of each device (the planes visible as lines 514 and 202 in FIG. 7B) are parallel, and in some cases coplanar. When telescoped, the planes formed by the flat portions of each device (the planes visible as lines 208 and 520) are parallel. As discussed at least in the method 1000 in FIG. 10, the endoscope 100 may be telescoped in the sheath 500 and may be removably mechanically coupled to one another.

Figure 8:
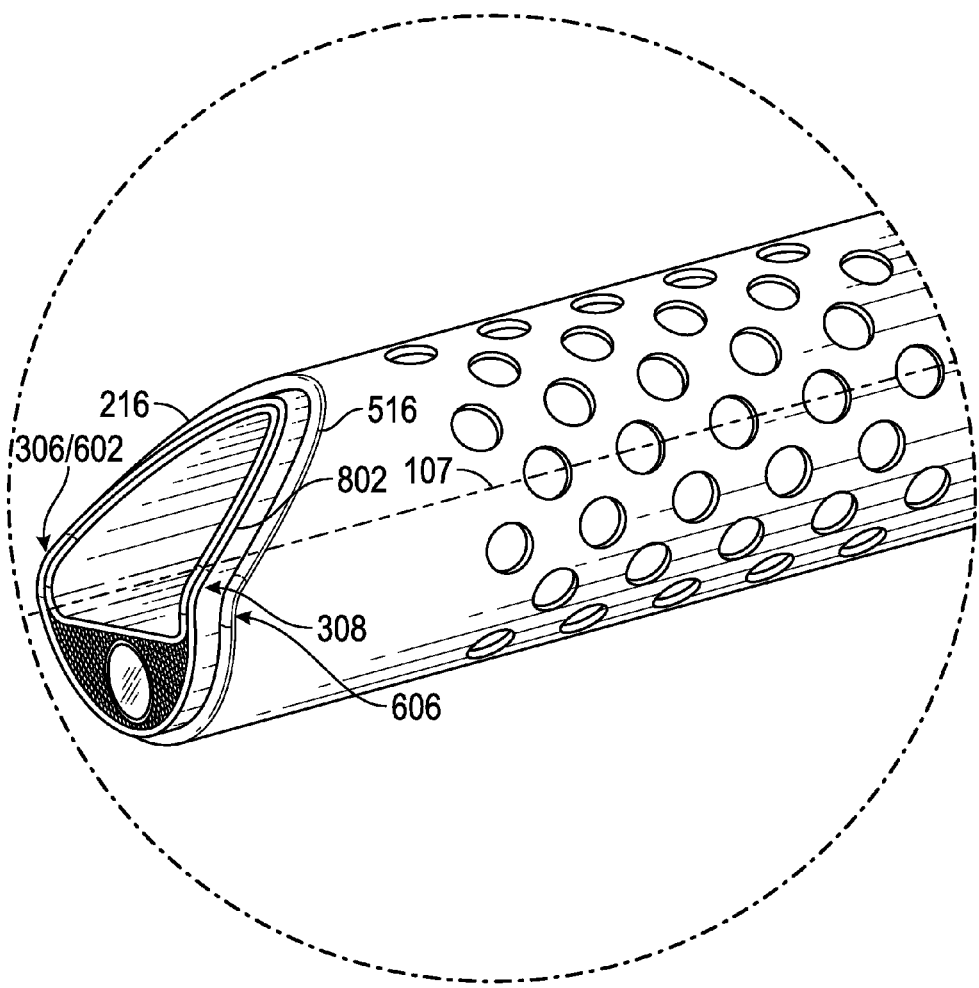
FIG. 8 shows a magnified partial-perspective view of an endoscope telescoped in a sheath in accordance with certain embodiments of the present disclosure.

FIG. 8 shows a magnified perspective view of the distal end of an example combination device 700A. In particular, FIG. 8 shows an example alignment of oblique portion 216 of the endoscope 100 and oblique portion 516 of the sheath 500. In particular, in the view of FIG. 8 the plane defined by the oblique portion 216 of the endoscope (the plane not specifically shown) and the planed formed by the oblique portion 516 of the sheath (the plane not specifically shown) are parallel. The parallel nature of the planes may be a design characteristic of the devices, or may stem from variations in length attributable to manufacturing tolerances. That is, though shown in large scale in FIG. 8, the distal tips of the devices are on the order of 5 mm in largest outside dimension. Having the planes defined by the oblique portions 216/516 be exactly coplanar be difficult in the defined scale, and thus as defined above coplanar includes the situation where planes defined by the oblique portions 216/516 are parallel and where the perpendicular distance between the planes is 0.5 millimeters or less. In addition to the alignment of the oblique portions 216 and 516, when telescoped the flat portions 518 and 228 are parallel as shown.

The devices discussed above may be manufactured and used alone and in combination according to various methods including but not limited to the methods discussed below in FIGS. 9 and 10.

Figure 9:
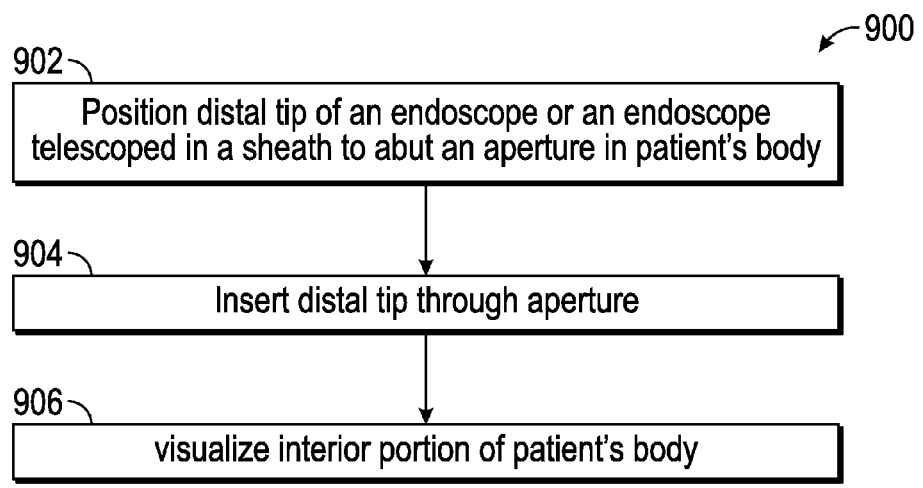
FIG. 9 is a flowchart of a method of using endoscopes and combination devices in accordance with certain embodiments of the present disclosure.

FIG. 9 shows a method 900 of use of an endoscope device. The example method 900 comprises positioning, at block 902, a distal tip of an endoscope to abut an aperture into a patient's body. The distal tip of the endoscope comprises an oblique portion which defines a plane that forms an angle with a central axis of the endoscope as discussed above. The distal tip of the endoscope may also comprise a flat portion which defines a second plane perpendicular to the central axis of the endoscope. At block 904, the distal tip of the endoscope is inserted through the aperture into the patient's body, using insertion force of less than 80% of an insertion force of an endoscope with a blunt front having the same outer dimension(s) (402, 416 in FIG. 2) as the endoscope. At block 906, an interior portion of the patient's body accessed through the aperture is visualized (e.g., by using a visualization conduit) at a viewing angle that is parallel to the central axis and may be referred to as a zero-degree angle. In some embodiments, inserting the distal tip at block 904 further comprises inserting the distal tip using the insertion force of less than 75% of an insertion force of an endoscope with a blunt front having the same outer dimension(s) (402, 416 in FIG. 2) as the endoscope. As discussed herein, an endoscope with a blunt front having the same outer dimensions is one that comprises an outer dimension the same as elongated shafts 108 and 508 discussed herein, and does not refer to a dimension of the oblique or flat portion of the distal tip 112/506.

In an example embodiment, positioning the distal tip at block 902 further comprises positioning the distal tip with the endoscope telescoped within a sheath. In this embodiment, the sheath comprises a first feature that defines a plane at least parallel (and possibly coplanar as defined) to the plane defined by the oblique portion of the endoscope, and the sheath has a second feature that defines a plane parallel to the plane defined by the flat portion of the endoscope. In the example embodiment, inserting the distal tip at block 904 further comprises simultaneously inserting both the sheath and the endoscope using an insertion force being less than 80% of an insertion force of a sheath and the endoscope with blunt fronts. In alternate embodiments, inserting the sheath and endoscope further comprises using an insertion force of less than 75% of an insertion force of a sheath and endoscope with blunt fronts. The combination device may employed in a variety of surgical procedures, including embodiments where positioning at block 902 further comprises positioning at a structure along a female genital tract of a patient, and in an alternate embodiment, positioning at block 902 further comprises positioning at the cervix of the patient.

In an alternate embodiment, at block 902, the distal tip of an endoscope is positioned to abut an aperture into a patient's body and comprises the oblique portion that defines a plane that forms an angle between and including 20 and 40 degrees with a central axis of the endoscope, and a flat portion that defines a plane perpendicular to the central axis of the endoscope. At block 904, the distal tip of the endoscope may be inserted through the aperture into the patient's body, and at block 906, an interior portion of the patient's body may be visualized at a viewing angle that is parallel to the central axis. In another example embodiment, inserting the distal tip at block 902 further comprises inserting with the oblique portion of the endoscope forming an angle of between and including 30 and 34 angular degrees, and in yet another alternate embodiment, inserting the distal tip further comprises inserting with the oblique portion of the endoscope forming an angle of about 32 angular degrees.

In some embodiments, positioning the distal tip at block 902 further comprises positioning the distal tip with the endoscope telescoped within a sheath along the central axis shared by the sheath and the endoscope. In this embodiment, the sheath comprises an oblique portion that defines a plane parallel (and in some cases coplanar s defined) with the plane defined by the oblique feature of the endoscope, and the sheath has a flat portion that defines a plane parallel with the plane defined by the blunt portion of the endoscope. In some embodiments, inserting the distal tip at block 904 further comprises simultaneously inserting both the sheath and the endoscope. In an embodiment, positioning at block 902 further comprises positioning at a structure along a female genital tract of a patient, and in an alternate embodiment positioning at block 902 further comprises positioning at the cervix of the patient.

Figure 10:
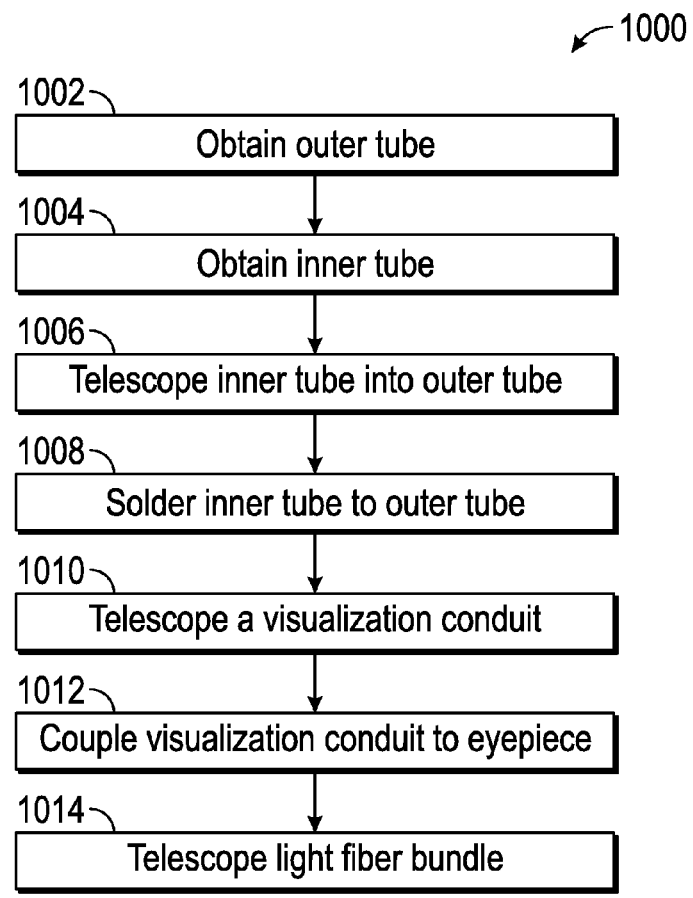
FIG. 10 is a flowchart of a method of fabrication of an endoscope in accordance with certain embodiments of the present disclosure.

FIG. 10 shows a method 1000 of fabricating an endoscope, such as example endoscope 100. The example method 1000 comprises assembling an endoscope by obtaining an outer tube at block 1002. The outer tube may comprise a first central axis, a first proximal end, and a first distal tip. An oblique portion at the first distal tip defines a plane that forms an angle of between and including 20 and 40 angular degrees to the first central axis, and a flat portion at the first distal tip that defines a plane perpendicular to the first central axis. In some embodiments, obtaining the outer tube at block 1002 further comprises obtaining an outer tube where the plane defined by the oblique portion forms an angle with the first central axis between and including 30 and 34 angular degrees, and in other embodiments obtaining the outer tube further comprises obtaining an outer tube where the plane defined by the oblique portion forms an angle of about 32 angular degrees.

The example method, at block 1004 further comprises obtaining an inner tube that comprises a second central axis, a second proximal end, and a second distal tip. In the example embodiment, an oblique portion at the second distal tip defines a plane that forms an angle of between and including 20 and 40 angular degrees to the second central axis, and a flat portion at the second distal tip that defines a plane perpendicular to the second central axis. In the example embodiment at block 1006, the method comprises telescoping the inner tube into the outer tube until the plane defined by the oblique portion of the outer tube is coplanar with the plane defined by the oblique feature of the inner tube. Moreover, telescoping the inner tube into the outer tube forms two channels within the outer tube, the first channel within the inner tube, and the second channel defined between the inner tube and an inside surface of the outer tube. In some embodiments, subsequent to telescoping the inner tube into the outer tube at block 1006, the method comprises soldering, at block 1008, the inner tube to the outer tube at the first distal and second distal tips and soldering the inner tube to the outer tube at the first and second proximal ends. At block 1010, a visualization conduit may be telescoped within the second channel and, at block 1012, the visualization conduit may be coupled to an eyepiece (e.g., a viewing port, such as 106 in FIG. 1). At block 1014, a light fiber bundle may be telescoped in the second channel with the visualization conduit and optically exposed at the plane defined by the blunt portion of the outer tube.

In some embodiments, obtaining the outer tube at block 1002 further comprises obtaining the outer tube that comprises: a first dimension measured perpendicularly to the first central axis, and the outer tube defines a second dimension measured perpendicularly to the first central axis and at a right angle to the first dimension, the second dimension equal to or smaller than the first dimension; a first transition area on a first side of the first distal tip between the first portion and the second portion of the outer tube, the first transition area smoothly varying between the first portion and the flat portion of the outer tube; a second transition area on a second side of the first distal tip opposite the first side, the second transition area smoothly varying between the first portion and the flat portion of the outer tube. In alternate embodiments, obtaining the outer tube at block 1002 further comprises obtaining the outer tube comprising the first transition area that defines a radius of curvature between and including 8% and 20% of the first dimension and comprising the second transition area that defines a radius of curvature between and including 8% and 20% of the first dimension.

In further example embodiments, obtaining the inner tube at block 1004 further comprises obtaining the inner tube that comprises: a third dimension measured perpendicularly to the second central axis, and the inner tube defines a fourth dimension measured perpendicularly to the second central axis and at a right angle to the third dimension, the fourth dimension equal to or smaller than the third dimension; a third transition area on a third side of the second distal tip between the first portion and the blunt portion of the inner tube, the third transition area smoothly varying between the first portion and the blunt portion of the inner tube; a fourth transition area on a second side of the second distal tip opposite the first side, the second transition area smoothly varying between the first portion and the blunt portion of the inner tube. In some embodiments, obtaining the inner tube at block 1004 comprises obtaining the inner tube comprising the third transition area defining a radius of curvature between and including 8% and 20% of the third dimension and comprising the fourth transition area that defines a radius of curvature between and including 8% and 20% of the fourth dimension.

In alternate embodiments, obtaining the inner tube at block 1004 further comprises obtaining the inner tube that comprises a cross-sectional shape perpendicular to the second central axis. The cross-sectional shape defines a straight portion and a curved portion coupled on each end to the straight portion, as well as a first height measured from an apex of the curved portion to the straight portion. In an embodiment, the first height is greater half the first dimension of the outer tube, but smaller than an internal dimension of the outer tube measured parallel to the first dimension. In various embodiments, at least one of the inner tube or an outer tube comprises a metallic material such as stainless steel, titanium, cobalt chrome, or combinations thereof.

EXAMPLES

Below are non-limiting examples of embodiments of endoscopes discussed herein. In order to establish that the angle of the oblique portion on the distal end of a device reduces insertion force (and therefore reduces trauma and/or pain) as compared to blunt front device, tests were performed to measure insertion forces for a series of different angles for the angle feature. In an embodiment, the testing discussed below employed a Mark-10 Series 5, 50 lb-f, 8000FZ, 25 KGF, 250N force gauge to measure insertion force though the rubber membrane held in a Cole-Parmer 06525-03 Test Fixture/Desiccator by McMaster p/n 5033A5 C-clamps.

The following table describes the equipment used in the testing:

TABLE 1

| Type of Equipment | Description | Model or ID No./ Serial Number |
|---|---|---|
| M5-50 Force gage | Mark-10 Series5/ 50 lbf, 8000FZ, 25 KGF, 250N | s/n 3479364 |
| Orb fixture | GYN Cut test fixture/Desiccator, | Cole-Parmer#06525-03 |
| C-Clamps | Steel C-clamp | Mcmaster carr# 5033A5 |

TABLE 1-continued

| Type of Equipment | Description | Model or ID No./ Serial Number |
|---|---|---|
| Rubber Test Coupons | 1" diameter, 0.125" thickness medical grade rubber membrane. | Fda-comliant Silicone Rubber, plain back ⅛" thick, 40a Durometer. |
| Angled Test Rods | Angled stainless steel rods with angled tip, 5 each of (20°, 30°, 35°, 45°, 60°, 90°) at 5.0 mm OD, and 5 each of (20°, 30°, 35°, 45°, 60°, 90°) at 5.6 and 5.0 mm OD. | Custom machined stainless steel angled rods. 304 stainless steel, medical grade. |

In particular, each of the test rods was inserted through the rubber test membrane while measuring the insertion forces. For each rod, the test was performed multiple times. The following tables provide example results:

TABLE 2

| Rod Tip Angle | Rod# | Run# 1 | 2 | 3 | 4 | 5 |
|---|---|---|---|---|---|---|
| 20° | 1 | 5.64 | 5.58 | 6.59 | 6.06 | 6.93 |
|  | 2 | 7.33 | 5.37 | 6.69 | 5.64 | 6.44 |
|  | 3 | 5.99 | 5.87 | 6.28 | 5.07 | 7.60 |
|  | 4 | 5.62 | 5.41 | 7.9 | 6.94 | 7.34 |
|  | 5 | 5.53 | 5.83 | 5.18 | 5.82 | 5.97 |
|  | Average | 6.02 | 5.61 | 6.53 | 5.91 | 6.86 |
|  | Overall Average | 6.1848 |  |  | STD | 0.664364 |

TABLE 3

| Rod Tip Angle | Rod# | Run# 1 | 2 | 3 | 4 | 5 |
|---|---|---|---|---|---|---|
| 30° | 1 | 6.48 | 6.56 | 6.63 | 7.1 | 6.36 |
|  | 2 | 6.73 | 6.63 | 6.48 | 5.92 | 6.18 |
|  | 3 | 5.87 | 6.37 | 6.65 | 7.34 | 7.14 |
|  | 4 | 6.29 | 6.39 | 7.49 | 7.28 | 7.18 |
|  | 5 | 7.26 | 6.89 | 6.92 | 7.13 | 6.13 |
|  | Average | 6.53 | 6.57 | 6.83 | 6.95 | 6.60 |
|  | Overall Average | 6.696 |  |  | STD | 0.317807 |

TABLE 4

| Rod Tip Angle | Rod# | Run# 1 | 2 | 3 | 4 | 5 |
|---|---|---|---|---|---|---|
| 35° | 1 | 8.52 | 8.03 | 9.37 | 7.07 | 8.33 |
|  | 2 | 8.53 | 7.95 | 7.96 | 8.45 | 7.82 |
|  | 3 | 9.3 | 8.85 | 8.95 | 7.8 | 8.37 |
|  | 4 | 7.48 | 8.67 | 8.16 | 6.79 | 8.12 |
|  | 5 | 8.21 | 8.54 | 8.99 | 8.09 | 8.02 |
|  | Average | 8.41 | 8.41 | 8.69 | 7.64 | 8.13 |
|  | Overall Average | 8.2548 |  |  | STD | 0.599056 |

TABLE 5

| Rod Tip Angle | Rod# | Run# 1 | 2 | 3 | 4 | 5 |
|---|---|---|---|---|---|---|
| 45° | 1 | 8.43 | 8.91 | 9.24 | 9.21 | 10.21 |
|  | 2 | 8.57 | 8.53 | 9.04 | 8.11 | 9.46 |
|  | 3 | 9.3 | 8.85 | 8.95 | 7.8 | 8.37 |
|  | 4 | 7.48 | 8.67 | 8.16 | 6.79 | 8.12 |
|  | 5 | 8.77 | 9.9 | 8.99 | 8.09 | 8.02 |

TABLE 5-continued

| Rod Tip Angle | Rod# | Run# | | | | |
|---|---|---|---|---|---|---|
| | | 1 | 2 | 3 | 4 | 5 |
| | Average | 8.51 | 8.97 | 8.88 | 8.00 | 8.84 |
| | Overall Average | 8.6388 | | | STD | 0.605667 |

TABLE 6

| Rod Tip Angle | Rod# | Run# | | | | |
|---|---|---|---|---|---|---|
| | | 1 | 2 | 3 | 4 | 5 |
| 60° | 1 | 10.53 | 9.98 | 10.43 | 9.87 | 9.72 |
| | 2 | 10.13 | 10.63 | 9.89 | 9.73 | 10.45 |
| | 3 | 10.53 | 9.72 | 7.46 | 8.91 | 9.65 |
| | 4 | 10.62 | 10.17 | 8.93 | 7.92 | 9.26 |
| | 5 | 9.83 | 10.23 | 10.52 | 9.92 | 9.82 |
| | Average | 10.33 | 10.15 | 9.45 | 9.27 | 9.78 |
| | Overall Average | 9.794 | | | STD | 0.346064 |

Figure 11:
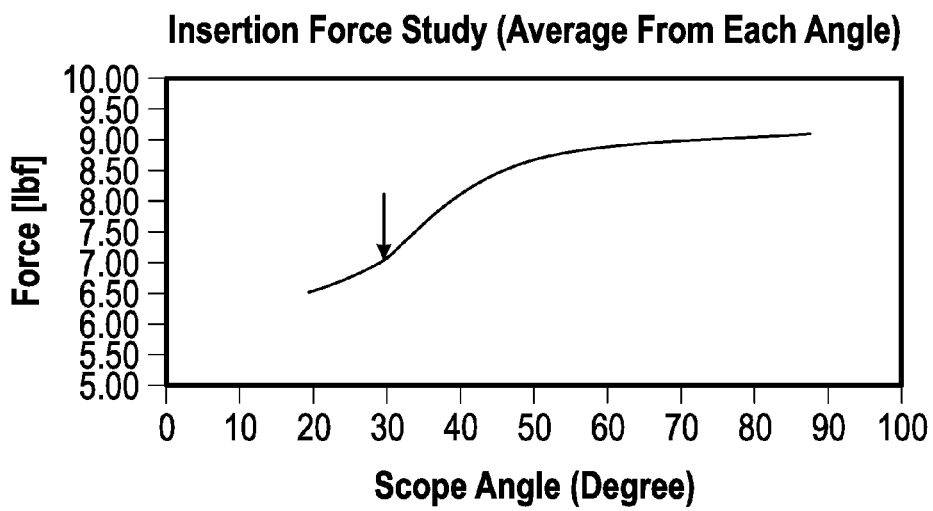
FIG. 11 shows a plot of insertion force as a function of angle of an oblique feature.

FIG. 11 is a plot that graphically shows the test results. In particular, FIG. 5 shows an inflection point at just over 30 angular degrees, where the insertion force as a function of diameter increases at a greater rate. Thus, for the further testing an angle of 32 angular degrees for the angle feature was selected.

The testing also tested insertion forces of endoscopes with and without sheaths. In particular, an endoscope with the oblique portions discussed above was tested with and without sheaths, and an endoscope with a blunt front (90° angle of the distal end to long central axis) was tested. The following table provides the results:

TABLE 7

| Real scope prototype | Force (lbf) Run#1 | Run#2 | Run#3 | Run#4 | Run#5 |
|---|---|---|---|---|---|
| No Sheath | | | | | |
| scope 1 | 4.73 | 5.25 | 5.61 | 5.72 | 5.16 |
| scope 2 | 5.73 | 5.28 | 4.83 | 5.39 | 5.08 |
| scope 3 | 5.56 | 4.92 | 5.72 | 4.87 | 4.28 |
| | | | | | avg 5.21 |
| | | | | | STD 0.428517 |
| With sheath | | | | | |
| scope 1 | 5.88 | 6.55 | 6.58 | 6.05 | 6.73 |
| scope 2 | 5.92 | 6.13 | 6.32 | 6.14 | 6.23 |
| scope 3 | 5.56 | 5.96 | 6.52 | 5.75 | 5.65 |
| | | | | | avg 6.13 |
| | | | | | STD 0.356448 |
| Normal 5.0 scope (Production) | | | | | |
| No Sheath | 7.43 | 7.51 | 6.78 | 6.76 | 7.43 |
| | | | | | avg 7.18 |
| | | | | | STD 0.377584 |
| With Sheath | 8.88 | 8.84 | 7.64 | 8.81 | 8.57 |
| | | | | | avg 8.55 |
| | | | | | STD 0.521795 |

% Diff No Sheath 27.5
% Diff with Sheath 28.3

As shown in Table 7, use of the oblique tip resulted in a 27.5% reduction in insertion force for endoscopes with no sheath, and a 28.3% reduction in insertion force for endoscopes including a sheath, compared to current endoscopes with blunt fronts (90° angle of the distal end to long central axis).

Exemplary embodiments are disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of broader terms such as "comprises," "includes," and "having" should be understood to provide support for narrower terms such as "consisting of," "consisting essentially of," and "comprised substantially of." Accordingly, the scope of protection is not limited by the description set out above but is defined by the claims that follow, that scope including all equivalents of the subject matter of the claims. Each and every claim is incorporated into the specification as further disclosure, and the claims are exemplary embodiment(s) of the present invention.

While exemplary embodiments of the invention have been shown and described, modifications thereof can be made by one skilled in the art without departing from the scope or teachings herein. The embodiments described herein are exemplary only and are not limiting. Many variations and modifications of the compositions, systems, apparatus, and processes described herein are possible and are within the scope of the invention. For example, while the first channel of the endoscope is described as being created within the inner tube telescoped within the outer tube, and with the second channel defined between the inner tube and the outer tube, in other embodiments the second channel may be created within the inner tube telescoped within the outer tube and with the second channel defined between the inner tube and the outer tube. Accordingly, the scope of protection is not limited to the exemplary embodiments described herein, but is only limited by the claims that follow, the scope of which shall include all equivalents of the subject matter of the claims. Unless expressly stated otherwise, the steps in a method claim may be performed in any order and with any suitable combination of materials and processing conditions.

What is claimed is:

1. An endoscope and sheath system comprising:
    an endoscope comprising:
        an endoscope elongated shaft that defines an endoscope central axis, an endoscope proximal end, and an endoscope distal tip, the endoscope elongated shaft defines a cross-section;
        an endoscope first portion of the endoscope distal tip defines a first plane that forms an angle of between and including 20 and 40 degrees to the endoscope central axis;

an endoscope second portion of the endoscope distal tip defines a second plane that is perpendicular to the endoscope central axis;

an endoscope first transition area on a first side of the endoscope distal tip between the endoscope first portion and the endoscope second portion, the endoscope first transition area varying between the endoscope first portion and the endoscope second portion;

an endoscope second transition area on a second side of the endoscope distal tip opposite the first side, the endoscope second transition area varying between the endoscope first portion and the endoscope second portion;

a first channel within the endoscope elongated shaft that terminates at the endoscope first portion;

a second channel within the endoscope elongated shaft that terminates at the endoscope second portion, the second channel fluidly isolated from the first channel along a length of the endoscope elongated shaft; and a visualization conduit that extends through the second channel, the visualization conduit optically exposed at the second plane such that a viewing angle through the visualization conduit is parallel to the endoscope central axis;

a sheath comprising:

a sheath elongated shaft that defines a sheath central axis, a sheath proximal end, and a sheath distal tip, the sheath elongated shaft defines a cross-section;

a sheath first portion of the sheath distal tip defines a third plane parallel to the first plane;

a sheath second portion of the sheath distal tip defines a fourth plane parallel to the second plane;

a sheath first transition area on a first side of the sheath distal tip between the sheath first portion and the sheath second portion, the sheath first transition area varying between the sheath first portion and the sheath second portion;

a sheath second transition area on a second side of the sheath distal tip opposite the first side, the sheath second transition area varying between sheath first portion and the sheath second portion;

at least one aperture defined through the sheath distal tip proximate to the sheath first portion; and an insertion port at the sheath proximal end of the sheath elongated shaft, the endoscope elongated shaft telescoped through the sheath insertion port.

2. The system of claim 1 further comprising:
the sheath first transition area abutting the endoscope first transition area; and
the sheath second transition area abutting the endoscope first transition area.

3. The system of claim 1 wherein the angle is between and including 30 and 34 degrees.

4. The system of claim 1 wherein the angle is about 32 degrees.

5. The system of claim 1 wherein the cross-sectional shape of the sheath elongated shaft is an elliptical cross-section.

6. The system of claim 1 further comprises a light fiber bundle in the second channel with the visualization conduit, the light fiber bundle optically exposed at the second plane.

7. The system of claim 1:
wherein the endoscope elongated shaft defines an endoscope largest outside dimension measured perpendicularly to the endoscope central axis, and the endoscope elongated shaft defines a further outside dimension measured perpendicularly to the endoscope central axis and at a right angle to the endoscope largest outside dimension, the further outside dimension equal to or smaller than the endoscope largest outside dimension; and
wherein the endoscope first transition area defines a radius of curvature between and including 8% and 20% of the endoscope largest outside dimension; and
wherein the endoscope second transition area defines a radius of curvature between and including 8% and 20% of the endoscope largest outside dimension.

8. The system of claim 7:
wherein the sheath elongated shaft defines a sheath largest outside dimension measured perpendicularly to the sheath central axis; and
wherein the sheath first transition area defines a radius of curvature between and including 8% and 20% of the sheath largest outside dimension; and
wherein the sheath second transition area defines a radius of curvature between and including 8% and 20% of the sheath largest outside dimension.

9. The system of claim 1 further comprising an endoscope third transition area on the endoscope first portion between the endoscope first and second transition areas, the endoscope third transition area smoothly varies from the first plane to an outside diameter of the endoscope elongated shaft.

10. The system of claim 1:
wherein the endoscope elongated shaft defines an endoscope largest outside dimension measured perpendicularly to the endoscope central axis, and the endoscope elongated shaft defines a further outside dimension measured perpendicularly to the endoscope central axis and at a right angle to the endoscope largest outside dimension, the further outside dimension equal to or smaller than the endoscope largest outside dimension; and
wherein the first channel further comprises:
a cross-sectional shape perpendicular to the endoscope central axis, the cross-sectional shape defines a straight portion parallel to the further outside dimension, and a curved portion coupled on each end to the straight portion; and
a first channel height measured from an apex of the curved portion to the straight portion;
wherein the first channel height is greater half the endoscope largest outside dimension, but smaller than an internal dimension of the endoscope elongated shaft measured parallel to the endoscope largest outside dimension.

* * * * *